(12) United States Patent
Magno et al.

(10) Patent No.: US 12,390,242 B2
(45) Date of Patent: Aug. 19, 2025

(54) METHOD TO IMPROVE CUTTING PERFORMANCE OF A MALLEABLE BLADE

(71) Applicant: GYRUS ACMI, INC., Westborough, MA (US)

(72) Inventors: Joey Magno, Dudley, MA (US); Reid M. Anderson, Lakeland, TN (US); Yoshinari Okita, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 170 days.

(21) Appl. No.: 17/644,202

(22) Filed: Dec. 14, 2021

(65) Prior Publication Data

US 2022/0218380 A1 Jul. 14, 2022

Related U.S. Application Data (60) Provisional application No. 63/135,297, filed on Jan. 8, 2021.

(51) Int. Cl.
*A61B 17/32* (2006.01)
*A61B 17/00* (2006.01)
(Continued)

(52) U.S. Cl.
CPC .......... *A61B 17/320016* (2013.01); *A61B 2017/00309* (2013.01); *A61B 2017/00946* (2013.01); *A61B 17/24* (2013.01); *A61M 25/0045* (2013.01)

(58) Field of Classification Search
CPC ...... A61B 17/320016; A61B 17/32002; A61B 2017/320032; A61B 2017/00309;
(Continued)

(56) References Cited

U.S. PATENT DOCUMENTS 5,178,158 A * 1/1993 de Toledo ......... A61M 25/0053
604/528
5,643,303 A 7/1997 Donahue
(Continued)

FOREIGN PATENT DOCUMENTS

AU 2015204376 A1 8/2015

OTHER PUBLICATIONS

"European Application Serial No. 22150117.4, Response filed Dec. 22, 2022 to Extended European Search Report mailed May 13, 2022", 2 pgs.

(Continued)

*Primary Examiner* — Brooke Labranche
*Assistant Examiner* — Christina C Lauer
(74) *Attorney, Agent, or Firm* — Schwegman Lundberg Woessner, P.A.

(57) ABSTRACT

Disclosed herein are systems and methods for a debrider blade assembly for improving cutting performance of a malleable blade. The system comprising of a malleable outer blade extending from a first end to a second end, an external surface and internal surface, the external surface including a plurality of openings and the internal surface defining an internal lumen. The system further comprising of a flexible inner blade at least partially disposed within the internal lumen of the outer blade, the flexible inner blade including a bendable segment formed from or covered by a flexible wrap. A covering member covering at least a portion of the flexible wrap or bendable segment of the flexible inner blade, and a helical coil extending around at least a portion of the covering member.

20 Claims, 9 Drawing Sheets

(51) Int. Cl.
   *A61B 17/24*   (2006.01)
   *A61M 25/00*   (2006.01)
(58) Field of Classification Search
   CPC ...... A61B 2017/00946; A61B 10/0266; A61B 10/0275
   See application file for complete search history.

(56) References Cited

U.S. PATENT DOCUMENTS

| | | | | |
|---|---|---|---|---|
| 5,658,264 | A * | 8/1997 | Samson | A61M 25/005 |
| | | | | 604/526 |
| 5,833,692 | A * | 11/1998 | Cesarini | A61B 17/32002 |
| | | | | 606/180 |
| 7,338,495 | B2 * | 3/2008 | Adams | A61B 17/32002 |
| | | | | 606/180 |
| 8,623,266 | B2 | 1/2014 | Adams | |
| 9,486,232 | B2 | 11/2016 | Heisler et al. | |
| 2008/0125799 | A1 | 5/2008 | Adams | |
| 2016/0174999 | A1 | 6/2016 | Casey et al. | |

OTHER PUBLICATIONS

"European Application Serial No. 22150117.4, Extended European Search Report mailed May 13, 2022", 8 pgs.
"European Application Serial No. 22150117.4, Communication Pursuant to Article 94(3) EPC mailed Dec. 7, 2023", 6 pgs.
"European Application Serial No. 22150117.4, Response filed May 31, 2024 to Communication Pursuant to Article 94(3) EPC mailed Dec. 7, 2023", 8 pgs.

* cited by examiner

METHOD TO IMPROVE CUTTING PERFORMANCE OF A MALLEABLE BLADE

CROSS-REFERENCE TO RELATED APPLICATION

This application claims the benefit of priority to U.S. Provisional Patent Application Ser. No. 63/135,297, filed Jan. 8, 2021, the contents of which were incorporated by reference herein in their entirety.

TECHNICAL FIELD

The present disclosure relates to a system for a debrider blade assembly, specifically a flexible/malleable blade assembly.

BACKGROUND

Ear Nose and Throat (ENT) debriders are commonly used to remove an amount of tissue or bone during a surgical procedure. Such procedures can include, for example, tonsillectomies, sinus surgery, or the like. Generally, a debrider includes a flexible blade attached to a handpiece that can rotate one or more rotating portions of the cutting portion of the blade. A portion of the blade can also be angled (e.g., bent at an angle relative to an axis) so as to position the cutting portion of the blade as desired or needed to reach, become oriented with, or the like, a piece, portion, or the like, of tissue.

SUMMARY

Debriders can be used in a variety of surgical procedures, such as ENT procedures such as a tonsillectomy, sinus surgery, or other similar procedures. Further, debriders can be used in procedures such as brain surgery, arthroscopy, or any procedure requiring use of a shaver blade or application. Often, during a surgical procedure, at least a portion of the blade of the debrider can be angled (e.g., bent) from a straight, zero degrees, to an angle such as fifteen degrees, thirty degrees, forty five degrees, ninety degrees, or the like. An issue that can arise is that the blade can be so stiff or rigid, that it is difficult to bend, and in the process of bending the blade, the blade can fail. Failures can include, for example, the blade unbending or even breaking, snapping, or the like, after it is bent multiple times, or bent at or past a particular angle.

One way to address these issues is to use an inner blade at least partially disposed within the internal lumen of the outer blade, with the inner and outer blades connected at an end (e.g., a proximal end) to a handpiece, housing, or the like, which can be operated by a surgeon. The inner and outer blades can be hollow metal tubes, made from, for example, surgical grade stainless steel, or another similar material capable of flexing or bending at an angle. In such a configuration, the inner blade can be caused to rotate, for example, via a motor connected to the handpiece, or the like. Further, the inner blade can include a port for suction, such as through tubing which connects to the handpiece/housing, which can allow a surgeon to pull tissue into the aperture of the blade to cut the tissue, and simultaneously remove tissue and blood from the surgical site. Adding an inner blade, however, can cause the blade assembly to be even more rigid or harder to bend, and can cause suction loss (e.g., loss of pressure) or cause leaking of blood and fluids.

Disclosed herein are systems and methods for a debrider blade assembly configured to address the issues such as those described above which can occur with malleable blades. In an example, a debrider blade assembly can include a malleable outer blade extending from a first end to a second end, an external surface and an internal surface. The external surface can include a plurality of openings, which can be a slit, aperture, crevice, incision, cleft, hole or the like, cut into the external surface of the outer blade, such as by using a laser cutting tool. The blade assembly can further include a flexible inner blade extending from a first end to a second end and including an external surface and an inner surface. The inner blade can be at least partially disposed, located, or the like, within the internal lumen of the outer blade. The inner blade can further include a bendable segment, which is at least partially formed from or covered with a flexible wrap (e.g., a triple wrap coil).

The blade assembly can further include a covering member, covering at least a portion of the flexible wrap forming or covering the bendable segment of the inner blade. In an example, the covering member can include a polyolefin wrap, or any similar material. A helical coil can be located, extended, wound around, or the like, at least a portion of the covering member on the inner blade.

The first end (e.g., a distal end) of the outer blade can include an outer cutting element. Similarly, the first end (e.g., a distal end) of the inner blade can include an inner cutting element. In an example, the first end of the outer blade, and in turn the outer cutting element can correspond, align, or the like, with the first end and inner cutting element of the inner blade. The blade assembly can be controllably connectable to a handpiece, the handpiece being connected to at least one of the inner blade or the outer blade (e.g., at the second end of at least one of the inner blade or the outer blade). At least a portion of the inner blade can be configured to transfer a torque from a motor connected to the handpiece to cause the inner blade to rotate.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The Outer Blade

Existing malleable debrider blades have a maximum bend angle relative to an axis that is not sufficient for certain procedures. The maximum bend angle is the angle at which attempting to further bend the blade causes the blade to break or otherwise fail. In order to cure this deficiency, a plurality of openings, slits, cuts, or the like can be made in the external surface of the blade to allow both for a larger bend radius about the axis, as well as increasing the amount of force which can be applied to the blade when causing the blade to bend within a plane at an angle. The number of openings can vary depending on the maximum bend angle sought to be achieved, the direction the blade is sought to bend, and the amount of rigidity/stiffness/softness of the bendable portion of the blade. The blade can include at least one opening to more than twenty openings.

In an example, the openings can have an axial spacing (e.g., a distance between adjacent openings on the surface of the outer blade), a depth (e.g., a distance into the surface of the outer blade that the opening extends), and a width (e.g., a distance between adjacent side walls or edges of the opening). Each of the axial spacing, depth and width of the openings can, alone or in some combination, control, affect, or the like, at least one of the amount of force required to bend the outer blade, the bend radius of the outer blade, or the maximum angle to which the outer blade can be bent. These features are illustrated in FIGS. 1-4 as described below.

Figure 1A:
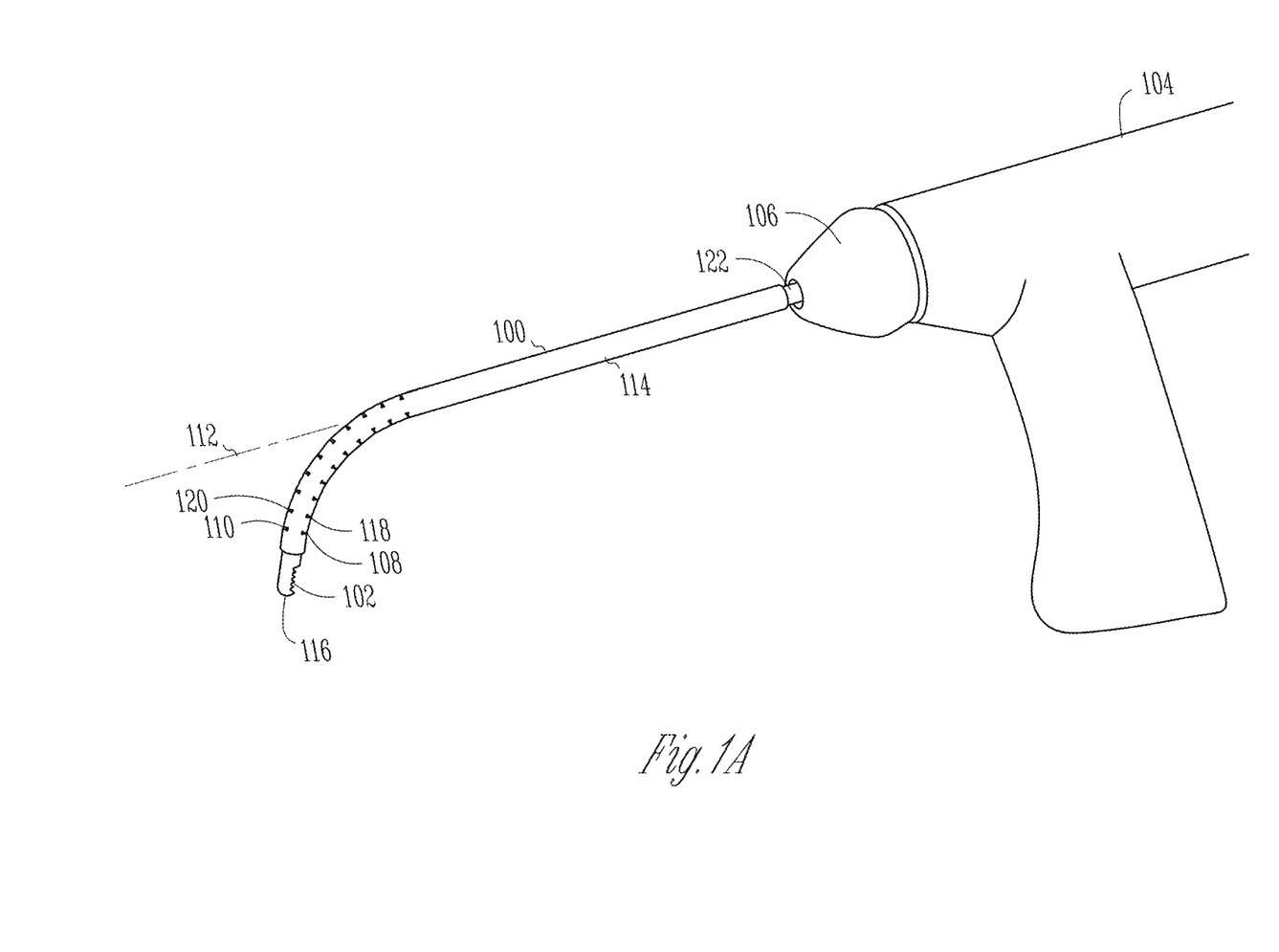
FIG. 1A illustrates an example of a debrider system including a malleable blade configured to bend relative to an axis, connected to a handpiece.

FIG. 1A illustrates an example of a debrider system including a malleable blade configured to bend relative to an axis, connected to a handpiece, handset, or the like. In the specific example of FIG. 1A, a malleable outer blade 100 can include a first end 116 with an outer cutting element 102 and a second end 122 attachable to a housing, such as a handpiece 104. The portion of the malleable outer blade 100 between the first end 116 and the second end 122 can be formed as a shaft substantially cylindrical in shape (e.g., a hollow cylinder), with an external surface 114, and a corresponding internal surface defining an internal lumen. Alternatively, the shaft of the malleable outer blade can define a shape that is oblong, polygonal, or the like. Furthermore, the shape can be regular or irregular. In an example, the cutting element 102 can be a serrated tooth cutting element. In another example, the cutting element 102 can be a straight blade. It is understood that the cutting element 102 can be any "end piece" suitable for attachment at the first end 116 of the malleable outer blade 100, capable of performing, accomplishing, or the like, a surgical function. In another example, outer blade can include an articulation portion configured to be manipulated and bent by surgeon instead of using the malleable outer blade 100. The articulation portion can include a wires and the wires can extend to the handpiece 104. The wires can be pulled or pushed for bending the articulation portion.

The malleable outer blade 100 can include a malleable segment between the first end 116 and a second end 122. The malleable segment can include a plurality of openings, such as slits 108, 110, 118, and 120 formed, cut, or the like, into the external surface 114 of the malleable outer blade 100. The malleable segment has a distal-most opening/slit and a proximal-most opening/slit. For example, slit 108 or 110 can be a distal-most opening/slit. A length of the malleable segment can be defined as a length between the distal-most opening/slit and the proximal-most opening/slit in a direction of a longitudinal axis 112. The handpiece 104 can include a rotating portion 106, which can be a knob, dial, or other similar actuation member capable of rotation. This can cause at least a portion of the outer blade 100 to rotate about longitudinal axis 112, such as a longitudinal axis of the outer blade 100. In an example, the outer blade 100 can be configured to bend within a plane at an angle relative to the longitudinal axis 112. For example, the outer blade 100 can be configured to bend at an angle between zero and ninety degrees relative to the longitudinal axis 112, such as in a left-to-right direction, right-to-left direction, up-and-down direction, or a combination thereof, and can be controlled by manipulation of the handpiece 104. In an example, the angle can be a maximum bend angle, which can be determined, at least in part, by the number of openings, such as slits 108, 110, 118, 120 formed on the external surface 114 of the outer blade 100.

Figure 1B:
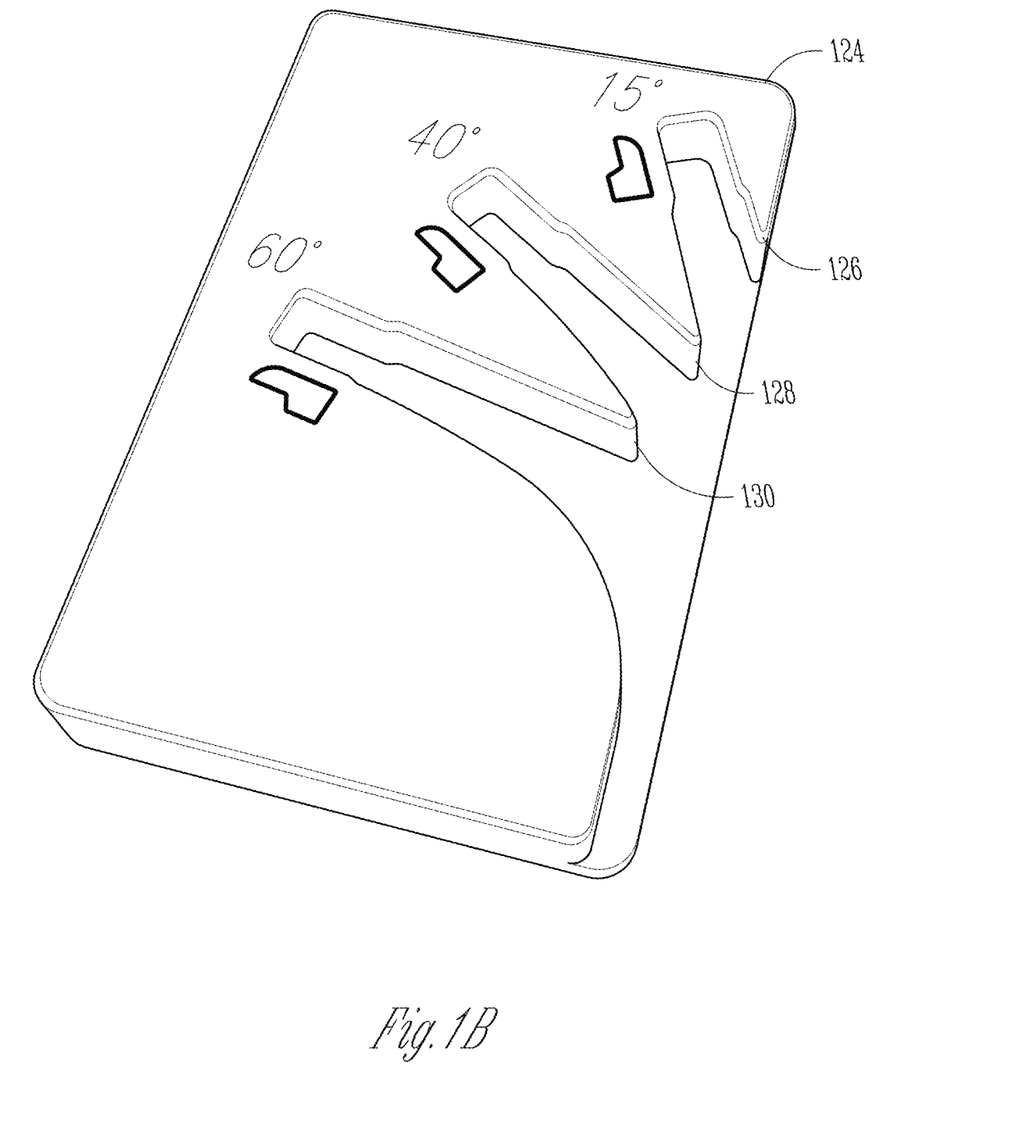
FIG. 1B illustrates an example of a bending fixture tool for bending a malleable blade.

FIG. 1B illustrates an example of a bending fixture tool for bending a malleable blade. In an example, the malleable outer blade 100 can be bent by using a bending fixture tool 124. In an example, the bending fixture tool 124 can be formed from a rigid material such as plastic, metal, a composite, or any other similar rigid material. In an example, the bending fixture tool 124 can include at least one opening, crevice, depression, impression 126-130, or the like, into which at least a portion of the malleable outer blade 100 (e.g., the first end 116 with the outer cutting element 102) can be inserted, located, placed, or the like so as to cause the malleable outer blade 100 to bend to an angle, such as 15 degrees, 40 degrees, sixty degrees, or the like. For example, depression 126 can correspond to an angle of fifteen degrees which is the angle to which the malleable outer blade 100 will be bent relative to the longitudinal axis 112. In an example, the bending fixture tool 124 can include a single depression such as 126-130 to allow the malleable outer blade to bend to a single particular angle, or as illustrated in FIG. 1B, the bending fixture tool can have multiple depressions such as 126-130 corresponding to different angle, as necessary or desired. Use of the bending fixture tool 124 can allow the malleable outer blade 100 to be bent to a desired angle without putting or prevent using excessive force when bending the malleable outer blade 100 and reduce the risk of the malleable outer blade 100 breaking or otherwise being compromised.

Figure 2:
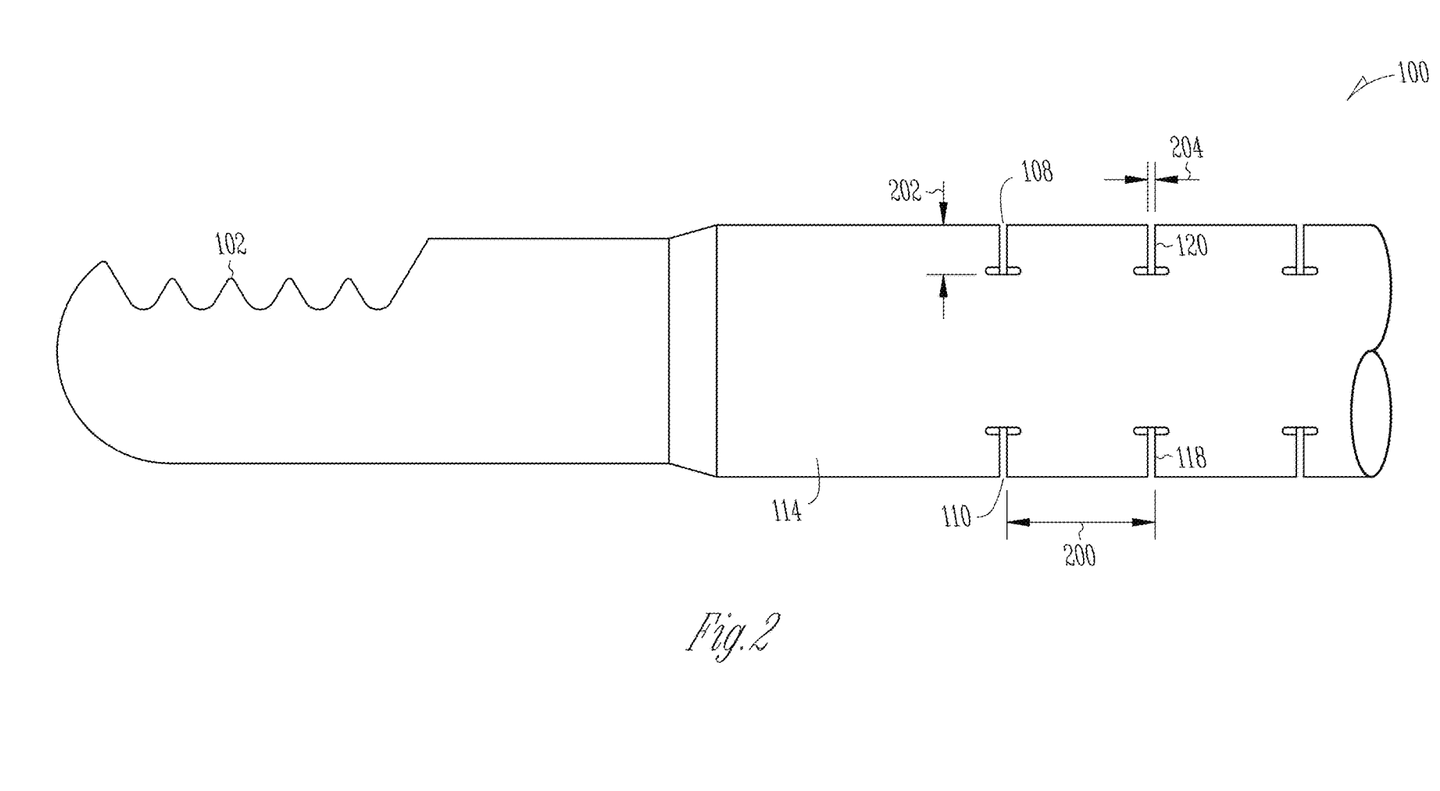
FIG. 2 illustrates an example of a malleable outer blade including slits extending into the external surface, and a cutting element.

FIG. 2 illustrates an enlarged side view of a portion of the malleable outer blade 100 of FIG. 1A. including the outer cutting element 102 and the slits 108, 110, 118, 120. The malleable outer blade 100 can include an axial spacing/distance 200 defined between adjacent openings on the external surface 114, such as between slits 110 and 118. The less/smaller the axial spacing 200 is, the higher the bend angle is when the length of the malleable segment is same. The axial spacing 200 can be a distance between 0.05 inches and 0.15 inches. For example, the axial spacing 200 between the adjacent slits can be a distance of about 0.08 inches, about 0.095 inches, or any distance suitable, desired, or the like, to meet a desired specification, quality, or the like, such as rigidity or maximum bend angle, or another quality of the malleable outer blade 100. The openings can also include a depth 202, which can be a distance the slits 108, 110, 118, or 120 are cut into the external surface 114, such as from an edge of the external surface 114 toward a center portion (e.g., toward the center of the external surface 114). The deeper the depth 202 is, the softer the outer blade 100 is. The depth 202 can be a distance between 0.02 inches and 0.09 inches. In an example, the depth 202 can be about 0.031 inches, about 0.042 inches, about 0.061 inches, or any suitable depth as desired or necessary to meet a requirement or specification of the malleable outer blade 100. In an example the openings can include a width/thickness 204, which can be a distance, space, thickness, or the like between a first edge and a second edge of the openings, such as slits 108, 110, 118, or 120. It is understood that the openings can have the same or a different axial spacing, depth, or thickness or combination thereof.

Figure 3:
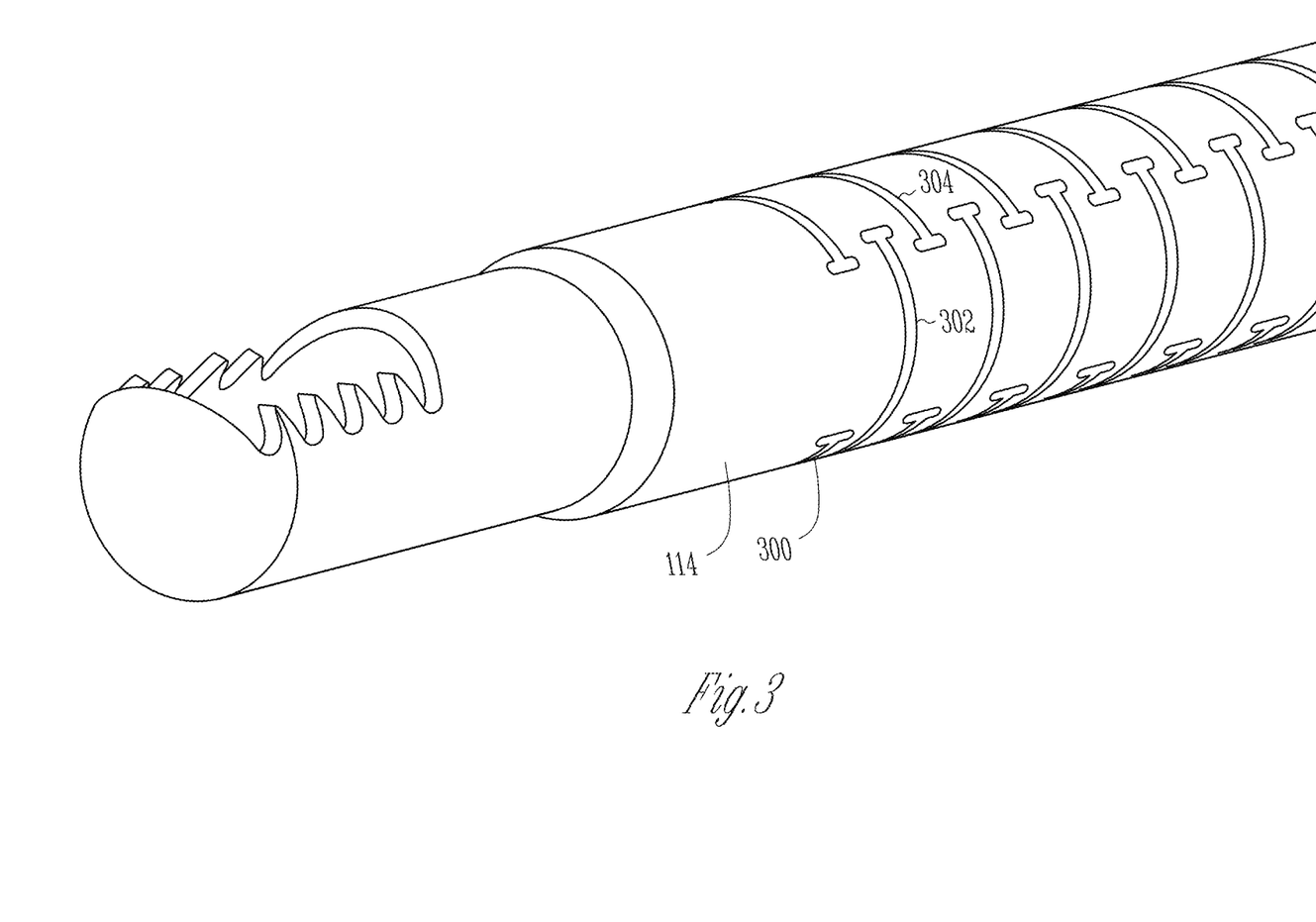
FIG. 3 illustrates an alternate example of an outer blade, illustrating an alternate arrangement of slits extending into the external surface of the outer blade.

In an example, the openings can be located on a first side and a second side of at least a portion of the external surface 114 of the malleable outer blade 100, and be located substantially across from each other, such as slits 108 and 110, and slits 118 and 120 in FIGS. 1 and 2. FIG. 3 illustrates an alternate example of an outer blade, illustrating an alternate arrangement of slits cut into the external surface of the outer blade.

In the example shown in FIG. 3, openings, such as slits 300, 302, and 304 can be located on the external surface 114 of the malleable outer blade 100 so as to be offset, staggered, or the like, such that slits such as 300 and 304 are substantially parallel to each other, and at least a portion of slit 302 is located between slits 300 and 304. Such a pattern of slits can be repeated along at least a portion of the length of the external surface 114 of the malleable outer blade 100. It is understood that the openings on the external surface 114 of the malleable outer blade 100 can be situated, cut, located, or the like in any configuration or combination of configurations as desired or necessary. Similarly, the depth 202 or width 204 of a particular opening or group of openings, as well as the axial spacing 200 between any two openings can be uniform, or varied as desired or necessary.

Figure 4:
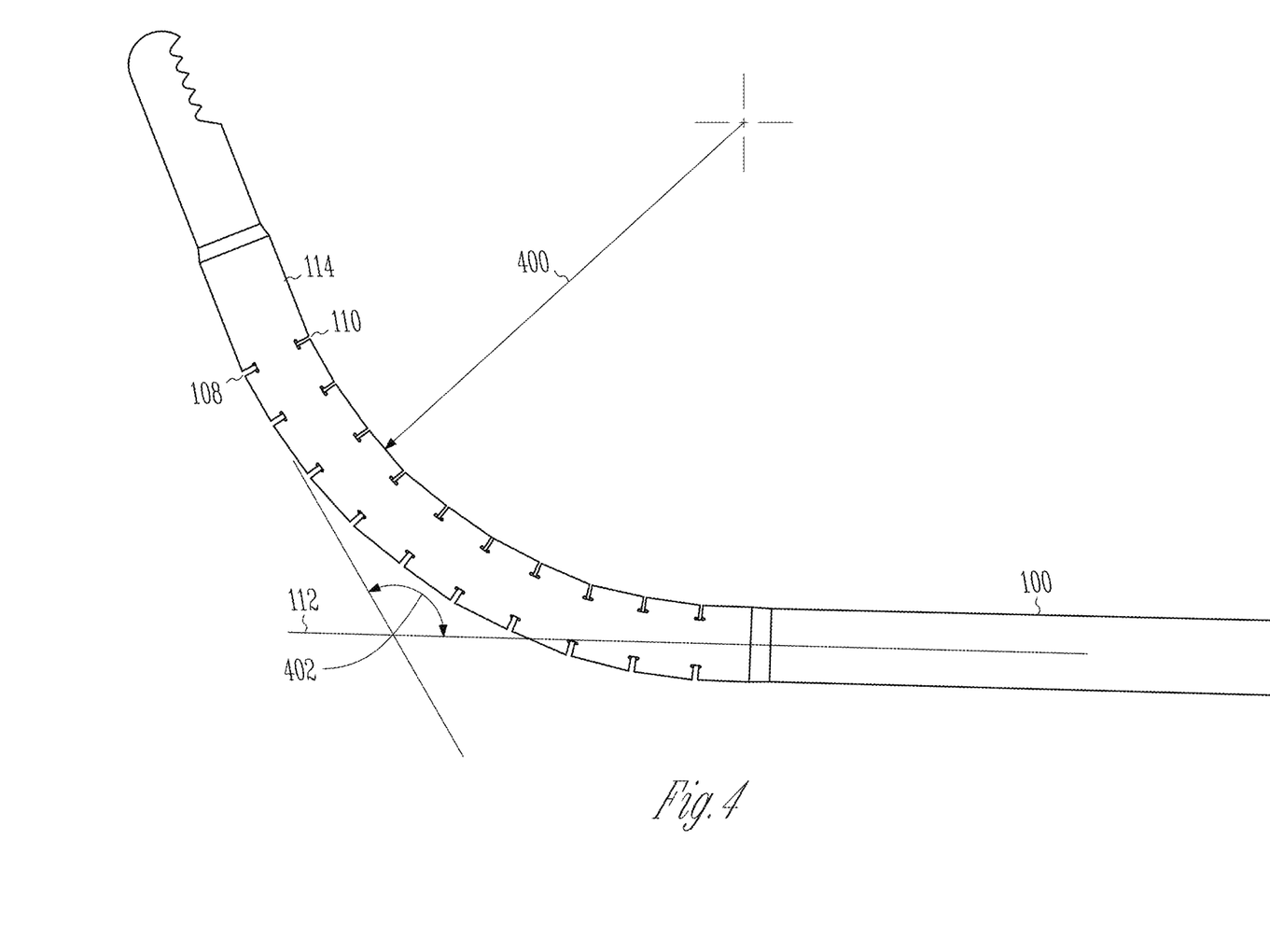
FIG. 4 illustrates an example of a malleable blade bent at an angle relative to an axis.

FIG. 4 illustrates an example of a malleable blade bent at an angle relative to a longitudinal axis. Two parameters that can be desired when performing a surgical procedure can be bend angle of the malleable outer blade 100, and the inner curve radius corresponding to the bend angle. In the example of FIG. 4, the malleable outer blade 100, is bent at an angle, a bend angle 402, relative to a longitudinal axis 112 of the malleable outer blade 100, such as the central longitudinal axis. In an example, the bend angle 402 can be an angle between zero degrees and ninety degrees, inclusive. In an example, the bend angle 402 can be a maximum angle (e.g., the largest angle) to which the malleable outer blade 100 can be bent without a failure, such as breaking, snapping, or the like, occurring. An inner bend radius 400 can correspond to a particular bend angle 402. The inner bend radius 400 can be formed by the radial distance that the malleable outer blade 100 is moved when the malleable outer blade is bent to a particular bend angle 402. In general, the smaller the axial spacing 200, the tighter the bend radius 400 will be. On the other hand, the larger the axial spacing 200 is, the larger the bend radius 400 will be. Table 1 below details particular maximum bend angles, bendable direction, and rigidity at particular depths, axial spacings, widths and number of openings/slits. Each number in the Table 1 is a targeted value by a simulation. Table 2 below details specific inner curve radii at particular maximum bend angles. Each number in the Table 2 is a measured value based on the each design in the Table 1. The maximum bend angle is an angle to which the malleable outer blade 100 can be bent to at least once before breaking. A distal side of the outer blade 100 is more difficult to be bent than the proximal side of the outer blade 100. As described hereinbefore, the deeper the depth 202 is, the softer the outer blade 100 is. The depth of openings/slits at a distal side of the malleable segment of the outer blade can be deeper than the depth of openings/slits at a proximal side of the malleable segment of the outer blade. In Design 4, the depth of openings/slits at a distal side of the malleable segment is 0.042 inches and the depth of openings/slits at a proximal side of the malleable segment is 0.031. As described hereinbefore, the smaller the axial spacing 200, the smaller the bend radius 400 is. In certain procedure, it might be useful that a bend radius of the distal side of the malleable segment of the outer blade is smaller than a bend radius of the proximal side of the malleable segment of the outer blade. The axial spacing of the openings/slits at a distal side of the malleable segment of the outer blade can be smaller than the axial spacing of openings/slits at a proximal side of the malleable segment of the outer blade. It is understood that the malleable outer blade 100 can be bent a single time, or, depending on the number of slits/openings, axial spacing, width, or a combination of one or more of each, can be bent multiple times as necessary or desired during a surgical procedure.

TABLE 1

| | Maximum Bend Angle (degrees) | Bendable Direction | Rigidity | Depth (inches) | Axial spacing (inches) | Width (inches) | Number of Slits |
|---|---|---|---|---|---|---|---|
| Design 1 | 90 | Up-Down | Harder | 0.031 | 0.08 | 0.005 | 20 |
| Design 2 | 60 | Up-Down | Harder | 0.031 | 0.095 | 0.005 | 11 |
| Design 3 | 60 | Up-Down | Softer | 0.042 | 0.095 | 0.005 | 11 |
| Design 4 | 60 | Up-Down | Medium | 0.042/0.031 | 0.095 | 0.005 | 11 |
| Design 5 | 90 | Up, Down, Left, and Right | Harder | 0.031 | 0.095 | 0.005 | 20 |

TABLE 2

|  | Design 1 | | Design 2 | | Design 3 | | Design 4 | |
| --- | --- | --- | --- | --- | --- | --- | --- | --- |
| Sample number | 1 | 2 | 1 | 2 | 1 | 2 | 1 | 2 |
| Maximum Bend Angle (degrees) | 96 | 102 | 59 | 57 | 59 | 61 | 61 | 60 |
| Inner Curve Radius (inches) | 0.812 | 0.797 | 0.979 | 1.004 | 0.924 | 0.952 | 0.909 | 0.866 |

The Inner Blade

The system can further include a flexible inner blade at least partially disposed, located, or the like, within the internal lumen (inside the hollow cylinder) of the outer blade. At least a portion of the inner blade (e.g., a bendable portion, bendable segment, or the like) can be formed from a flexible wrap (e.g., a triple coil wrap). The triple coil wrap can be formed from a flexible/bendable metal (e.g., stainless steel, steel, or the like) or composite material capable of bending at the angle of the outer blade, as well as rotate (by transferring a torque from a rotating portion of the handpiece 104 described above, oscillating, or moving in another similar manner as necessary or desired.

The system can also be configured to produce a suction pressure on the inner blade to allow the inner blade to "pull in" a piece of tissue to be cut, or aspirate to clear a field of fluid such as blood. By using a flexible wrap to form a portion of the inner blade, suction pressure can be reduced due to the flexible wrap not being fully sealed. To remedy this loss of suction pressure, at least a portion of the inner blade (e.g., the bendable segment formed from the flexible wrap) can be covered with a covering member, such as a polyolefin wrap or another similar "shrink wrap" material, which can "seal" the inner blade and reduce or eliminate the loss of suction pressure.

When a covering member such as a polyolefin wrap is used to cover the inner blade, the edges of the laser cut openings can rub against the wrap (because of the outer diameter of the inner blade rubbing against the inner diameter of the outer blade) causing the covering member to rip, shred, tear, or otherwise be similarly compromised. The tearing of the covering member can again reduce, lower, inhibit, or the like, the suction pressure, which can cause less tissue to be drawn into the "cutting window" of the blades, thereby decreasing the amount of tissue aspiration, resulting in poor overall cutting performance.

Methods such as attempting to electro-polish the edges, corners, or the like, of the openings or the entire inner diameter/inner lumen of the outer blade to reduce the amount of sharp edges by smoothing the surface of the outer blade can be beneficial but can still result in the covering member on the inner blade being torn and thus reducing performance of the system. Likewise, attempting to use a coating to "fill" the openings and thus provide a smoother surface upon which the covering member of the inner blade can contact, rub, or the like, can reduce the malleability of the outer blade, and hinder the bendability of the outer blade as it becomes too stiff. To cure this issue, a helical coil can be extended around at least a portion of the covering member covering the inner blade, providing a surface between the covering member and the inner diameter of the outer blade which can prevent the covering member from being compromised, and as such mitigate or eliminate the loss of suction pressure.

Figure 5A:
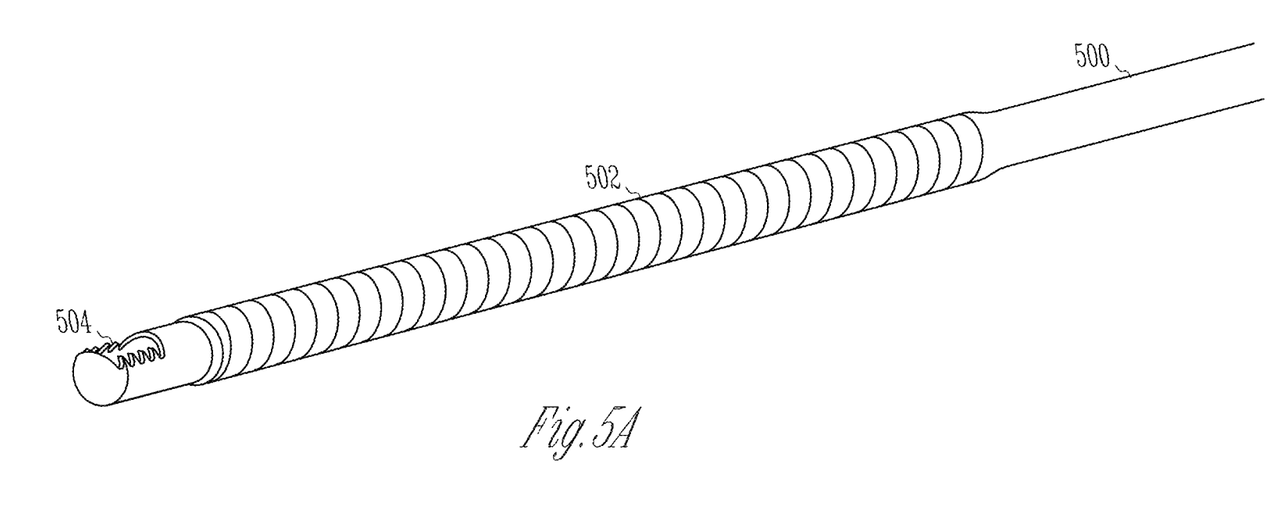
FIGS. 5A and 5B illustrates an example of a flexible inner blade with a flexible wrap forming at least a part of a bendable portion of the inner blade.
Figure 5B:
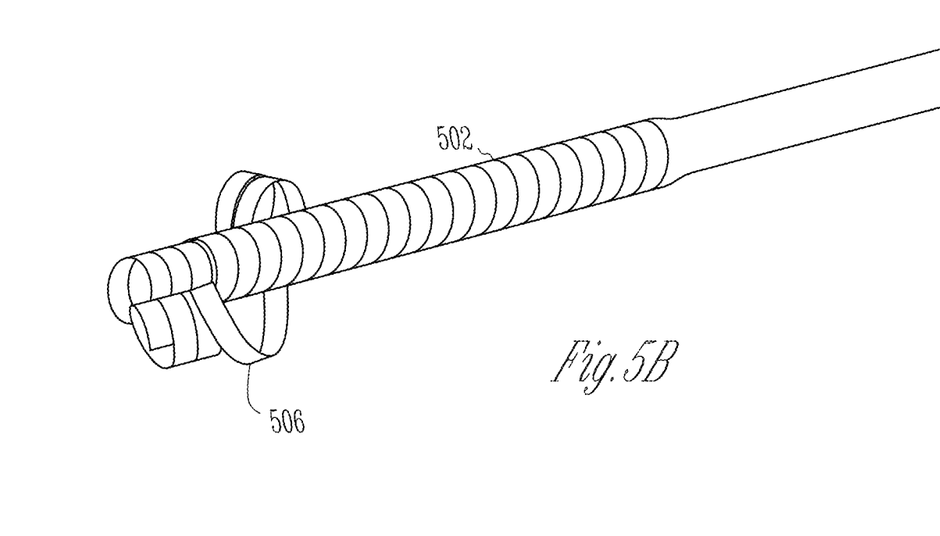

FIGS. 5A and 5B illustrates an example of a flexible inner blade extending from a first end to a second end, with a flexible wrap forming at least a part of a bendable portion of the inner blade. FIG. 5B specifically shows how the flexible wrap is wrapped, turned, or the like. In an example, a flexible inner blade 500 can include a bendable segment 502, As shown in FIG. 5B, the bendable segment 502 can be formed from a flexible wrap, such as a triple wrap coil which can be wrapped, turned, wound, or the like, together using strips/bands/layers 506, or the like, of the flexible wrap to form a substantially cylindrical shaped bendable segment 502. The bendable segment 502, can allow the flexible inner blade to bend as the malleable outer blade 100 is bent to an angle relative to the longitudinal axis 112.

The flexible inner blade 500 can be configured to have an outer diameter sufficient so that the flexible inner blade 500 can be at least partially disposed within the internal lumen of the outer blade (e.g., 0.122 inches). The flexible inner blade can also include an inner cutting element 504 on an end (e.g., the first end) which can be a serrated cutting element, or any other suitable cutting element, and can correspond to the outer cutting element 102 on the first end 116 of the malleable outer blade 100. In an example, the second end of the flexible inner blade 500 can be connected, attached, or the like, to a housing, such as handpiece 104. In an example, at least a portion of the flexible inner blade 500, such as the bendable segment 502 can be configured to transfer a torque from the handpiece 104, such as from a motor connected to handpiece 104. In another example, the inner cutting element 504 can be a burr instead of the serrated cutting element.

Figure 6:
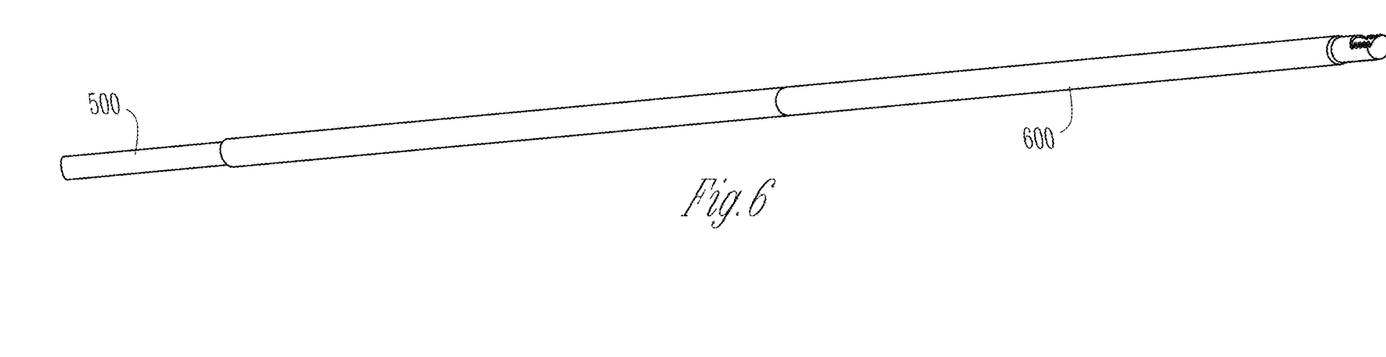
FIG. 6 illustrates an example of a flexible inner blade containing a covering member covering at least a part of the bendable portion.

FIG. 6 illustrates an example of a flexible inner blade containing a covering member covering at least a part of the bendable portion. In the example of FIG. 6, at least a portion of the flexible inner blade 500, such as the bendable segment 502 can be covered with a covering member 600. In an example, the covering member can be a polyolefin wrap, or any other similar material capable of "sealing" the flexible wrap forming the bendable segment 502 of the flexible inner blade 500. The thickness of the covering member 600 can be selected so as to leave a clearance between the outer diameter of the flexible inner blade 500, and the inner diameter of the malleable outer blade 100 so as to allow the flexible inner blade 500 to turn, rotate, oscillate, reciprocate, or the like, within the inner lumen of the flexible outer blade 100.

Figures 7A, 7B:
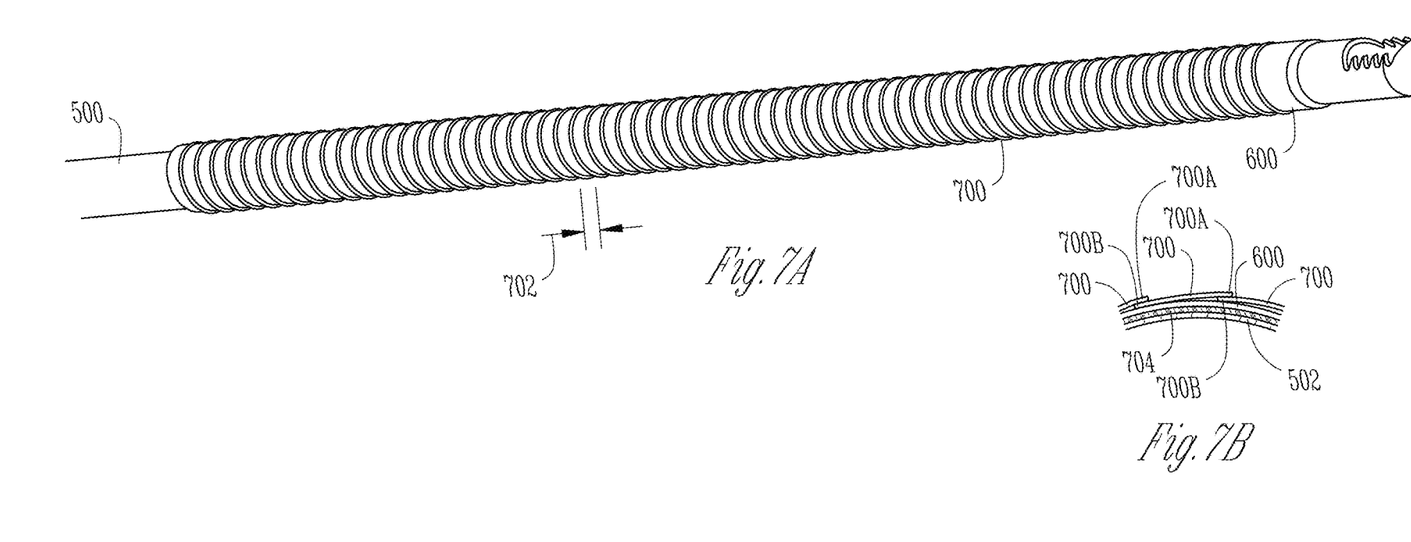
FIG. 7A illustrates an example of a helical coil extending around at least a portion of the covering member illustrated in FIG. 6
FIG. 7B illustrates an example cross-section of the inner blade showing a bendable portion of the inner blade covered by a flexible wrap, the covering member of FIG. 6, and the helical coil of FIG. 7A.

FIG. 7A illustrates an example of a helical coil extending around at least a portion of the covering member illustrated in FIG. 6 and FIG. 7B illustrates an example cross-section of the inner blade showing a bendable portion of the inner blade covered by a flexible wrap, the covering member of FIG. 6, and the helical coil of FIG. 7A. In an example, a helical coil 700 can be located on at least a portion of the covering member 600. The helical coil 700 can have a diameter between 0.005 inches and 0.008 inches. In an example, the helical coil 700 can be a 0.005 inch diameter hardened spring wire material (e.g., an SS304 hardened spring wire) or any other similar material. The helical coil 700 can form a barrier, cushion, layer, or the like, of between the covering member 600 of the flexible inner blade 500 and the inner lumen, inner surface, interior, or the like, of the malleable outer blade 100, so as to keep the covering member 600 from contacting (e.g., rubbing) the inner lumen, inner surface, interior, or the like, of the malleable outer blade. This can protect the covering member against being torn, ripped, or otherwise damaged by any part of the malleable outer blade 100. In this example, the helical coil 700 is exemplified as a protecting member for protecting the covering member 600, but one or more rings can be attached around at least a portion of the covering member 600 instead of the helical coil 700 for the same purpose.

In an example, the helical coil 700 can include a pitch 702 between adjacent coil turns. The pitch 702 can be between 0.02 inches and 0.1 inches. In an example, the pitch 702 can be variable along the length of the helical coil 700. For example, the pitch 702 toward an end of the helical coil 700 can be finer than the pitch 702 in the middle of the helical coil. In general, the finer the pitch 702 between the adjacent turns of the helical coil 700, the stiffer/harder to bend, the flexible inner blade 500 will be.

In an example, the helical coil 700 can be wound around a mandrel, shaft, spindle, support, rod, shaft, or the like, with a diameter smaller than the outer diameter of the flexible inner blade 500 with the covering member 600 in place. Then, the helical coil 700 can be installed by re-winding the helical coil 700 over the covering member 600 (e.g., turn by turn) or threading/screwing the helical coil 700 onto the covering member 600. This can cause the helical coil 700 from tangling against the openings such as slits 108, 110, 118, or 120, as the individual coil turns of the helical coil 700 can pass through the openings of the malleable outer blade 100. Further, by first winding the helical coil 700 around a mandrel with a smaller diameter than the outer diameter of the flexible inner blade 500 can allow the helical coil 700 to grab, attach, grip, catch, capture, or the like the covering member tightly without a need to provide any other method to fasten, anchor, or the like, the helical coil 700 to its position on the covering member 600.

In an example, the bendable segment 502 of the flexible inner blade 500 can be formed by a flexible wrap or as illustrated in FIG. 7B, the bendable segment 502 (or a portion thereof) can be covered with a flexible wrap 704. The flexible wrap 704, can, in turn, be covered by the covering member 600, which can then be wrapped in the helical coil 700 with edges 700A and 700B of the helical coil 700 overlapping with portions of the helical coil 700 as it wraps around the covering member 600.

Figure 8:
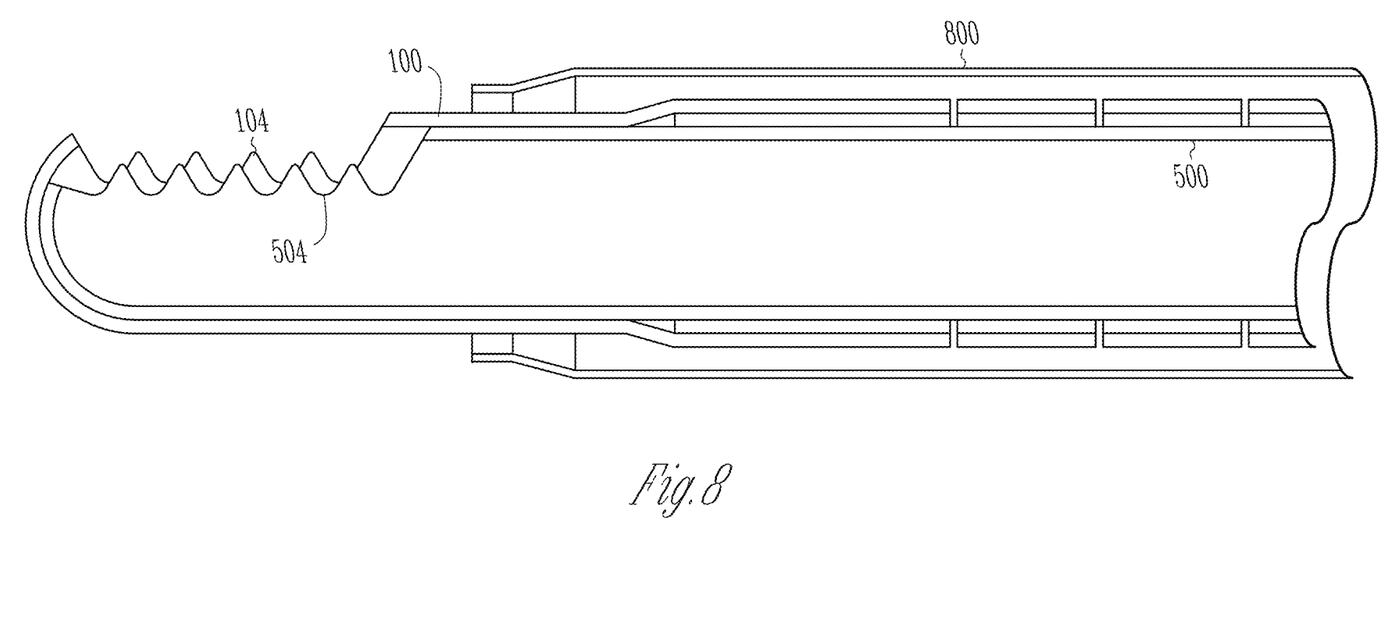
FIG. 8 illustrates an example of a portion of a debrider blade assembly including an outer blade, and an inner blade disposed within the internal lumen of the outer blade.

FIG. 8 illustrates an example of a portion of a debrider blade assembly including an outer blade, and an inner blade disposed within the internal lumen of the outer blade. In the example of FIG. 8, the flexible inner blade 500 can be seated, located, or the like, within the internal lumen of the malleable outer blade 100. The flexible inner blade 500 can also be located within the malleable outer blade 100 so that the inner cutting element 504 is aligned with the outer cutting element 102 such as to form a cutting area or window in which the inner cutting element 504 can be moved in conjunction with or relative to the outer cutting element 102. For example, the inner cutting element 504 can rotate as the flexible inner blade 500 is rotated using the handpiece 104.

Figure 9:
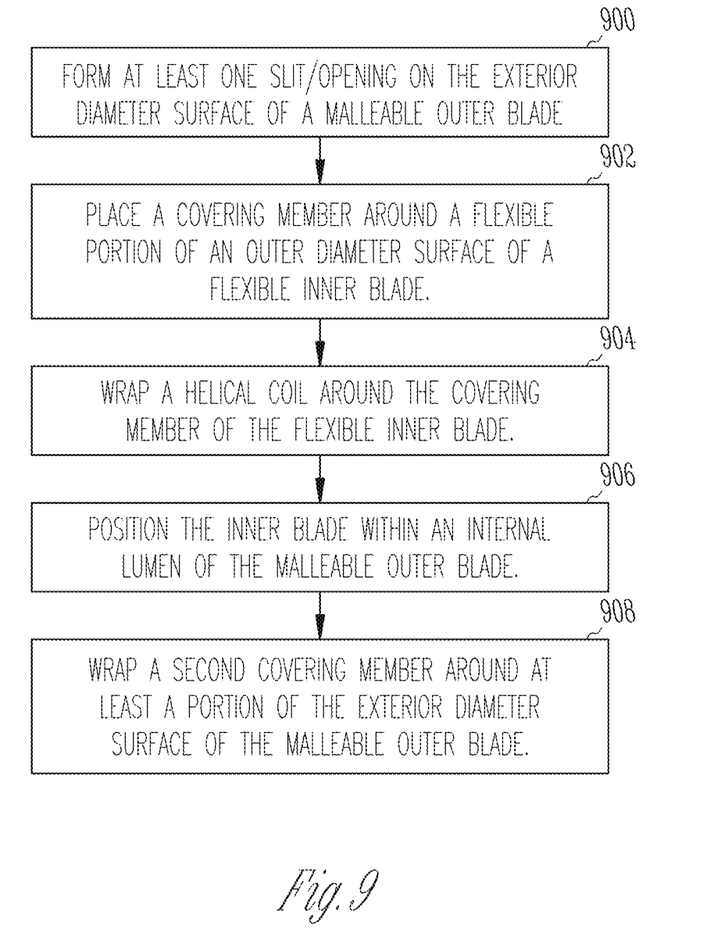
FIG. 9 illustrates a flowchart showing an example method for improving cutting performance of a malleable blade.

In an example, the system can include a second covering member 800 located around at least a portion of external surface (e.g., the outer diameter) of the malleable outer blade 100. In an example, the second covering member can be a polyolefin wrap, similar to the covering member 600 located around the flexible inner blade 500. In an example, the second covering member 800 can be a heat shrink tube, or any similar covering. In an example, the second covering member 800 can be positioned so as to cover at least two of the openings of the plurality of openings such as slits 108 and 110, or 118 and 120. Including the second covering member 800 on the outside of the malleable outer blade, can improve the suction pressure of the system FIG. 9 illustrates a flowchart showing an example method for manufacturing or assembling a flexible blade system. Operation 900 can include forming at least one slit/opening on the exterior diameter surface of a malleable outer blade, such as malleable outer blade 100 as described above. In an example, the openings can be slits, such as 108, 110, 118, or 120 as described above, extending along a portion of the malleable outer blade to allow the outer blade to more easily bend when manipulated by a surgeon either before or during a surgical procedure, such as by manipulating the outer blade using a handpiece to which the outer blade is connected.

Operation 902 can include placing a covering member around a flexible portion of an outer diameter surface of a flexible inner blade. In an example, the flexible inner blade can include a flexible wrap on at least a portion of an outer diameter surface. In an example, the flexible wrap can be a triple coil wrap which can form at least a portion of the outer diameter surface of the flexible inner blade, forming a bendable segment of the flexible inner blade which allows the flexible inner blade to move as the malleable outer blade is bent at an angle relative to a longitudinal axis of the malleable outer blade.

In an example, the covering member can be a polyolefin wrap, or another similar shrink wrap capable of creating a seal around the flexible wrap or bendable segment of the flexible inner blade. Creating a seal around the bendable segment can allow the system to maintain suction pressure when suction is applied through the flexible inner blade, such as through a handpiece connected to at least one of the malleable outer blade or the flexible inner blade.

Operation 904 can include locating a helical coil on at least a portion of the covering member. The helical coil can allow the flexible inner blade to move (e.g., rotate) within the inner diameter of the malleable outer blade without the covering member contacting (e.g., rubbing against) the inner diameter of the malleable outer blade, causing the covering member to tear, rip, shred, or otherwise become compromised, which can result in a loss of suction pressure.

Operation 906 can include positioning the inner blade within an internal lumen of the malleable outer blade. In an example, the flexible inner blade can be located within a portion of an inner diameter (e.g., an inner lumen) of the malleable outer blade. For example, the malleable outer blade can be formed as a hollow cylinder into which the flexible inner blade can be inserted, slipped, or the like. In an example, the flexible inner blade can be located such that a first and second end of the flexible inner blade corresponds to a first and second end of the malleable outer blade, and that the first end of the flexible inner blade include an inner cutting element corresponding to an outer cutting element on the first end of the malleable outer blade.

Operation 908 can include wrapping a second covering member, such as a polyolefin wrap, around at least a portion of the outer diameter surface of the malleable outer blade. For example, the second covering member can be wrapped around the portion of the outer diameter surface containing the plurality of openings, to further seal the system and further reduce, lessen, or the like, the loss of suction pressure. The second covering member at Operation 908 can be an optional step, as the malleable outer blade can remain uncovered, as necessary or desired.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

ADDITIONAL NOTES AND EXAMPLES (Example 1) A surgical device, comprising:
an outer tube including an external surface and an internal surface, and the internal surface defining an internal lumen;
an inner tube including an external surface and an internal surface, the inner tube at least partially disposed within the internal lumen of the outer tube, and the inner tube including a flexible segment,
a cover covering the flexible segment; and
a protecting member extending around at least a portion of the cover so as to keep the cover from contacting the internal surface of the outer tube.

(Example 2) The surgical device of example 1, wherein the outer tube is malleable.

(Example 3) The surgical device of example 1, wherein the outer tube includes an articulation portion configured to be bent.

(Example 4) The surgical device of example 1, wherein the external surface of the outer tube including a plurality of openings.

(Example 5) The surgical device of example 4, wherein the plurality of openings are slits extending through the outer tube from the external surface to the internal surface.

(Example 6) The surgical device of example 1, wherein the inner tube includes a flexible wrap.

(Example 7) The surgical device of example 6, wherein the flexible wrap includes a coil wrap.

(Example 8) The surgical device of example 1, wherein the inner tube includes a helical cut.

(Example 9) The surgical device of example 1, wherein the cover includes heat shrink tube.

(Example 10) The surgical device of example 1, wherein the cover includes a polyolefin wrap.

(Example 11) The surgical device of example 1, wherein the protecting member includes a helical coil extending around at least a portion of the cover.

(Example 12) The surgical device of example 1, wherein the protecting member includes one or more rings attached around at least a portion of the cover.

(Example 13) The surgical device of example 1, wherein the outer tube includes an outer cutting element.

(Example 14) The surgical device of example 1, wherein the outer cutting element includes a serrated tooth cutting element.

(Example 15) The surgical device of example 1, wherein the inner tube includes an inner cutting element.

(Example 16) The surgical device of example 1, wherein the inner cutting element includes a serrated tooth cutting element.

(Example 17) The surgical device of example 1, wherein the inner cutting element includes a burr.

(Example 18) The surgical device of example 1, wherein at least a portion of the outer tube is configured to bend within a plane at an angle.

(Example 19) The surgical device of example 18, wherein the angle is between zero degrees and ninety degrees relative to a longitudinal axis of the outer tube.

(Example 20) The surgical device of example 1, further comprising:
a second cover covering at least a portion of the external surface of the outer tube.

(Example 21) The surgical device of example 1, wherein the second cover includes a polyolefin wrap.

(Example 22) The surgical device of example 1, wherein the surgical device is controllably connectable to a handpiece, wherein the handpiece is connected to at least one of the outer tube or the inner tube, and wherein at least a portion of the inner tube is configured to transfer a torque from a motor connected to the handpiece.

(Example 23) The surgical device of example 1, further comprising:
a handpiece controllably connectable to the surgical device, wherein the handpiece is connected to at least one of the outer tube or the inner tube, and wherein at least a portion of the inner tube is configured to transfer a torque from a motor connected to the handpiece.

(Example 24) The surgical device of example 1, wherein the protecting member includes a distal portion and a proximal portion, wherein the cover extends proximally beyond the proximal portion of the protecting member in a longitudinal axis of the inner tube.

(Example 25) The surgical device of example 1, wherein the protecting member includes a distal portion and a proximal portion, wherein the cover extends distally beyond the distal portion of the protecting member in a longitudinal axis of the inner tube.

(Example 26) The surgical device of example 1, wherein the flexible segment includes a distal portion and a proximal portion, wherein the cover extends proximally beyond the proximal portion of the flexible segment in a longitudinal axis of the inner tube.

(Example 27) The surgical device of example 1, wherein the flexible segment includes a distal portion and a proximal portion, wherein the cover extends distally beyond the distal portion of the flexible segment in a longitudinal axis of the inner tube.

(Example 28) The surgical device of example 1, wherein the outer tube includes a malleable segment having a distal side and a proximal side, wherein the malleable segment includes a plurality of openings, wherein the plurality of openings includes a first opening at the distal side of the malleable segment and a second opening at the proximal side of the malleable segment, wherein a depth of the first opening is deeper than a depth of the second opening.

(Example 29) The surgical device of example 1, wherein the outer tube includes a malleable segment having a distal side and a proximal side, wherein the malleable segment includes a plurality of openings, wherein the plurality of openings includes a first adjacent openings at the distal side of the malleable segment and a second adjacent openings at the proximal side of the malleable segment, wherein an axial spacing between the first adjacent openings is smaller than a axial spacing between the second adjacent openings.

(Example 30) The surgical device of any of examples 1-29 further comprising a bending fixture tool configured to bend the outer tube to an angle.

(Example 31) A surgical device, comprising:
an outer tube including an external surface and an internal surface, and the internal surface defining an internal lumen;
an inner tube including an external surface and an internal surface, the inner tube at least partially disposed within the internal lumen of the outer tube, and the inner tube including a flexible segment, and
wherein the outer tube includes a malleable segment having a distal side and a proximal side, the distal side of the malleable segment is softer than the proximal side of the malleable segment.

(Example 32) The surgical device of example 31, wherein the malleable segment includes a plurality of openings, wherein the plurality of openings includes a first opening at the distal side of the malleable segment and a second opening at the proximal side of the malleable segment, wherein a depth of the first opening is deeper than a depth of the second opening.

(Example 33) A surgical device, comprising:
an outer tube including an external surface and an internal surface, and the internal surface defining an internal lumen;
an inner tube including an external surface and an internal surface, the inner tube at least partially disposed within the internal lumen of the outer tube, and the inner tube including a flexible segment, and
wherein the outer tube includes a malleable segment having a distal side and a proximal side, a bend radius of the distal side of the malleable segment is smaller than a bend radius of the proximal side of the malleable segment.

(Example 34) The surgical device of example 33, wherein the malleable segment includes a plurality of openings, wherein the plurality of openings includes a first adjacent openings at the distal side of the malleable segment and a second adjacent openings at the proximal side of the malleable segment, wherein an axial spacing between the first adjacent openings is smaller than a axial spacing between the second adjacent openings.

What is claimed is:
1. A debrider blade assembly, comprising:
an outer blade extending from a first end to a second end and including an external surface and an internal surface, the external surface including a plurality of openings, and the internal surface defining an internal lumen;
an inner blade extending from a first end to a second end and including an external surface and an internal surface, the inner blade at least partially disposed within the internal lumen of the outer blade, and the inner blade including a bendable segment, wherein a flexible wrap at least one of: forms or covers at least a portion of the bendable segment;
a covering member covering at least a portion of the flexible wrap; and
a helical coil extending around at least a portion of the covering member, wherein the helical coil is interposed as a barrier between the covering member and the internal lumen of the outer blade and prevents direct contact therebetween, and wherein the helical coil includes a winding such that the winding passes through the plurality of openings of the outer blade and inhibits the covering member from tangling with the plurality of openings in the internal surface of the outer blade.

2. The debrider blade assembly of claim 1, wherein the plurality of openings are slits extending through the outer blade from the external surface to the internal surface.

3. The debrider blade assembly of claim 1, wherein the first end of the outer blade includes an outer cutting element.

4. The debrider blade assembly of claim 3, wherein the first end of the inner blade includes an inner cutting element.

5. The debrider blade assembly of claim 4, wherein at least one of the outer cutting element or the inner cutting element is a serrated tooth cutting element.

6. The debrider blade assembly of claim 1, wherein at least a portion of the outer blade is configured to bend within a plane at an angle.

7. The debrider blade assembly of claim 6, wherein the angle is between zero degrees and ninety degrees relative to a longitudinal axis of the outer blade.

8. The debrider blade assembly of claim 1, wherein the covering member is a polyolefin wrap, and wherein the helical coil is formed from a hardened spring wire.

9. The debrider blade assembly of claim 1, further comprising:
a second covering member covering at least a portion of the external surface of the outer blade.

10. The debrider blade assembly of claim 9, wherein the second covering member is a polyolefin wrap.

11. The debrider blade assembly of claim 1, wherein the debrider blade assembly is controllably connectable to a handpiece, wherein the handpiece is connected to at least one of the outer blade or the inner blade, and wherein at least a portion of the inner blade is configured to transfer a torque from a motor connected to the handpiece.

12. A method for improving cutting performance of a malleable blade, the method comprising:
locating a plurality of openings on an outer blade;
locating an inner blade within a portion of an inner diameter of the outer blade, the inner blade including a flexible wrap on at least a portion of an outer diameter surface of the inner blade;
wrapping a covering member around at least a portion of the flexible wrap on the outer diameter surface of the inner blade; and
locating a helical coil on a least a portion of the covering member, wherein the helical coil is interposed as a barrier between the covering member and the inner diameter of the outer blade and prevents direct contact therebetween, and wherein the helical coil includes a winding such that the winding passes through the plurality of openings of the outer blade and inhibits the covering member from tangling with the plurality of openings in an internal surface of the outer blade.

13. The method of claim 12, wherein the outer blade includes a first and second end, wherein the inner blade has a first end and a second end corresponding to the first and second end of the outer blade, wherein the first end of the outer blade includes a cutting element and the first end of the inner blade includes a cutting element corresponding to the cutting element of the outer blade, wherein at least a portion of the inner blade is configured to transfer a torque from a motor included in a handpiece, and wherein the handpiece is controllably connected to at least one of the outer blade or the inner blade.

14. The method of claim 13, wherein at least one of the cutting element of the inner blade or the cutting element of the outer blade is a serrated tooth cutting element.

15. The method of claim 12, wherein the plurality of openings are slits located on a first side and a second side of at least a portion of the outer blade, and wherein a first slit on the first side is located substantially across from a second slit on the second side.

16. The method of claim 12, wherein at least a portion of the outer blade is configured to bend within a plane at an angle wherein the angle is between zero degrees and ninety degrees relative to a longitudinal axis of the outer blade.

17. The method of claim 12, wherein the covering member is a polyolefin wrap, and wherein the helical coil is formed from a hardened spring wire.

18. The method of claim 12, further comprising:
wrapping a second covering member around at least a portion of an outer diameter surface of the outer blade.

19. A system for a debrider blade assembly, comprising:
an outer blade and an inner blade operably connected to a handpiece, the outer blade including a plurality of openings located on an outer diameter surface, and the inner blade located within at least a portion of an inner diameter of the outer blade, wherein the outer blade is configured to bend in a plane at an angle between zero degrees and ninety degrees relative to a longitudinal axis of the outer blade, wherein the outer blade includes a serrated cutting element on a first end, wherein the inner blade includes a serrated cutting element on a first end corresponding to the serrated cutting element on the outer blade, and wherein the inner blade is configured to transfer a torque from the handpiece;
a flexible wrap forming at least a portion of an outer diameter surface of the inner blade;
a polyolefin wrap located on at least a portion of the outer diameter surface of the inner blade;
a helical coil formed from a hardened spring wire located over at least a portion of the polyolefin wrap, wherein the helical coil is at least one of wound or threaded over the polyolefin wrap, wherein the helical coil is interposed a barrier between the polyolefin wrap and the inner diameter of the outer blade and prevents direct contact therebetween and wherein the helical coil includes a pitch between adjacent coil turns; and
a covering member located on at least a portion of the outer diameter surface of the outer blade, wherein the covering member is located so as to cover at least two of the plurality of openings, and wherein the helical coil includes a winding such that the winding passes through the plurality of openings of the outer blade and inhibits the covering member from tangling with the plurality of openings in an internal surface of the outer blade.

20. The system of claim 19, wherein the plurality of openings are slits located on a first side and a second side of at least a portion of the outer blade, and wherein a first slit on the first side is located substantially across from a second slit on the second side.

\* \* \* \* \*

UNITED STATES PATENT AND TRADEMARK OFFICE
CERTIFICATE OF CORRECTION

| | |
|---|---|
| PATENT NO. | : 12,390,242 B2 |
| APPLICATION NO. | : 17/644202 |
| DATED | : August 19, 2025 |
| INVENTOR(S) | : Magno et al. |

Page 1 of 1

It is certified that error appears in the above-identified patent and that said Letters Patent is hereby corrected as shown below:

In the Claims

In Column 14, Line 64, in Claim 12, delete "a" and insert --at-- therefor

Signed and Sealed this
Seventh Day of October, 2025

John A. Squires
*Director of the United States Patent and Trademark Office*